United States Patent [19]

Asaoka et al.

[11] Patent Number: 5,399,784
[45] Date of Patent: Mar. 21, 1995

[54] PROCESS FOR THE PRODUCTION OF BISPHENOL A

[75] Inventors: Sachio Asaoka, Yokohama; Noriyuki Yoneda; Kouji Sakashita, both of Tokyo; Tetsuo Maejima, Kiyose; Makoto Yasui; Akio Shindo, both of Yokohama, all of Japan

[73] Assignee: Chiyoda Corporation, Yokohama, Japan

[21] Appl. No.: 125,137

[22] Filed: Sep. 23, 1993

Related U.S. Application Data

[63] Continuation of Ser. No. 872,727, Apr. 22, 1992, abandoned.

[30] Foreign Application Priority Data

| Aug. 5, 1991 | [JP] | Japan | 3-219164 |
| Aug. 5, 1991 | [JP] | Japan | 3-219165 |
| Oct. 11, 1991 | [JP] | Japan | 3-292213 |

[51] Int. Cl.6 .............................................. C07C 39/16
[52] U.S. Cl. ..................................... 568/728; 568/724; 568/749
[58] Field of Search .......................... 568/724, 728, 749

[56] References Cited

U.S. PATENT DOCUMENTS

| 3,290,390 | 12/1966 | Prahl | 568/724 |
| 3,936,507 | 2/1976 | Ligorati et al. | |
| 4,327,229 | 4/1982 | Mendiratta | 568/749 |
| 4,517,387 | 5/1985 | Matsunaga et al. | 568/728 |
| 4,942,265 | 7/1990 | Iimuro et al. | 568/724 |

FOREIGN PATENT DOCUMENTS

| 1231991 | 5/1971 | United Kingdom . |
| 1381398 | 1/1975 | United Kingdom . |

OTHER PUBLICATIONS

European Search Report dated Aug. 20, 1993.

*Primary Examiner*—Johann Richter
*Assistant Examiner*—John Peabody
*Attorney, Agent, or Firm*—Armstrong, Westermann, Hattori, McLeland & Naughton

[57] ABSTRACT

A high quality bisphenol A with a high purity and an excellent hue is produced from a crystalline adduct of bisphenol A and phenol by washing the adduct with specifically purified phenol, followed by decomposition of the washed adduct to separate bisphenol A. The purification is performed by a method including contacting raw material phenol with a strong-acid ion exchange resin to obtain treated phenol, and distilling the treated phenol.

3 Claims, No Drawings

PROCESS FOR THE PRODUCTION OF BISPHENOL A

This application is a continuation of application Ser. No. 07/872,727, filed Apr. 22, 1992, now abandoned.

This invention relates to a process for the production of bisphenol A having a high purity and a low tendency to color.

Bisphenol A (2,2-bis(4'-hydroxyphenyl)propane) is an important raw material for polycarbonate resins and epoxy resins and there is an increasing demand for high quality bisphenol A. In particular, it is highly desirable to provide colorless, transparent, high purity bisphenol A as a raw material for polycarbonate resins to be used for the preparation of optical parts.

One well known process for the production of bisphenol A includes reacting acetone with a stoichiometrically excess amount of phenol in the presence of an acid catalyst. With respect to the recovery of bisphenol A from the reaction product, a method is known in which the reaction product is cooled for the crystallization of a bisphenol A-phenol adduct and the resulting adduct is subsequently decomposed into bisphenol A and phenol.

The known process involves a problem that bisphenol A produced contains impurities. Such impurities include those already colored and those colored with time. As a result, bisphenol A obtained by the above method is colored and the color becomes deep with time.

To cope with this problem, U.S. Pat. No. 4,942,265 proposes a method in which a crude adduct of phenol and bisphenol A is washed with liquid phenol obtained by decomposition of the phenol-bisphenol A adduct such as by distillation, extraction or steam stripping. This method, however, has the following problems. Namely, phenol obtained by distillation or steam stripping of the adduct contains impurities derived from the adduct, such as chroman and 2,4'-bisphenol A, and impurities formed during the distillation or stripping step, such as isopropenyl phenol. The contamination of the latter impurities is significant when a high distillation temperature is used. Thus, the use of such phenol for the washing of the adduct fails to give colorless, high purity bisphenol A. When solvent extraction is adopted for the decomposition of the adduct, it is necessary to separate the solvent from the phenol before the use of the phenol for washing the adduct. The phenol after the separation treatment, however, still contains a small amount of the solvent. Thus, the use of such phenol for the washing of the adduct prevents the recycling of the phenol after the washing to, for example, the reaction stage.

The present invention has been made with the foregoing problems of the known process in view. In accordance with one aspect of the present invention there is provided a process for the production of bisphenol A, wherein a crystalline adduct of bisphenol A and phenol is washed with phenol and is then treated to separate bisphenol A therefrom, characterized in that, as at least part of the phenol for use in the washing of said adduct, purified phenol obtained by contacting raw material phenol with a strong-acid ion exchange resin followed by distillation is used, said raw material phenol including at least one member selected from the group consisting of (A) phenol for industrial use, (B) phenol separated from a reaction product of phenol and acetone, (C) phenol separated from a crystallization product of bisphenol A-containing phenol and (D) phenol used for washing a crystalline adduct.

In another aspect, the present invention provides a process for the production of bisphenol A, comprising the steps of:

(a) reacting acetone with a stoichiometrically excess amount of phenol to obtain a bisphenol A-containing product;

(b) crystallizing said product to obtain a crystalline adduct of bisphenol A and phenol;

(c) providing raw material phenol which contains an impurity forming a high boiling point material having a boiling point of higher than 185° C. upon being heated at a temperature higher than the melting point of phenol;

(d) contacting said raw material phenol with a sulfonic acid-type cation exchange resin at a temperature and for a period of time sufficient to convert at least part of said impurity into said high boiling point material and to obtain treated phenol;

(e) distilling said treated phenol at a temperature of 185° C. or less to separate purified phenol, as distillate, from said high boiling point material;

(f) washing said adduct with said purified phenol; and (g) decomposing said washed adduct to obtain bisphenol A.

The present invention also provides a method of purifying raw material phenol which contains an impurity forming a high boiling point material having a boiling point of higher than 185° C. upon being heated at a temperature higher than the melting point of phenol and which has a water content of not greater than 0.5% by weight, comprising the steps of:

contacting said raw material phenol with a strong-acid ion exchange resin at such a temperature as to convert at least part of said impurity into said high boiling point material and to obtain treated phenol; and distilling said treated phenol at a temperature of 185° C. or less to separate phenol as distillate from said high boiling point material.

The present invention will now be described in detail below.

The crystalline adduct of bisphenol A and phenol to be used in the process of the present invention may be produced by any known manner, such as by a method in which acetone is reacted with excess phenol in the presence of an acid catalyst to obtain a bisphenol A-containing product, the product being thereafter subjected to crystallization conditions to crystallize bisphenol A as an adduct with phenol.

The crystalline adduct is then washed with specifically purified phenol. Since generally available phenol contains an impurity, such as benzofurane and derivatives thereof and aromatic aldehydes and derivatives thereof, which is responsible for the coloring of bisphenol A, it is essential to remove or reduce such an impurity prior to the use thereof for washing the crystalline adduct.

The raw material phenol to be purified is one which contains an impurity convertible to a high boiling point material having a boiling point of at least about 185° C. upon being heated at a temperature higher than the melting point of phenol and is preferably selected from (A) phenol for industrial use, (B) phenol separated from a reaction product of phenol and acetone, (C) phenol separated from a crystallization product of bisphenol A-containing phenol and (D) phenol used for washing a crystalline adduct. The raw material phenol preferably has a purity of at least 99% by weight, more preferably at least 99.5% by weight.

Commercially available phenol of an industrial use grade with a purity of 99.5% or more may be suitably used as above phenol (A).

After completion of the reaction of acetone with phenol, the product is generally subjected to a separation treatment for removing a part of unreacted phenol therefrom. The phenol thus recovered may be used as raw material phenol (B).

The product obtained by reaction of acetone with phenol is treated to form a crystalline adduct of bisphenol A and phenol. Crystallization is generally performed at a temperature of about 41°–80° C. After crystallization, the mixture is subjected to solid-liquid separation to separate the mixture into a crystalline adduct and a mother liquor. Generally, such crystallization and solid-liquid separation is repeated several times. Thus, phenol is recovered as a mother liquor in each of the solid-liquid separation stages. Such recovered phenol may be used as raw material phenol (C). The phenol recovered in the initial crystallization and separation step is preferably used.

Phenol which has been used for washing the crystalline adduct is recovered. Such phenol may be suitably reused, after being purified, for washing the adduct. Thus, phenol recovered in the washing step may be used as raw material phenol (D).

The purification of above raw material phenol (A)–(D) is performed as follows. The raw material phenol is first contacted with a strong-acid ion exchange resin, generally a sulfonic acid-type ion exchange resin, such as a sulfonated styrene-divinylbenzene copolymer, a sulfonated, cross-linked styrene polymer, a phenol-formaldehyde-sulfonic acid resin or a benzene-formaldehyde-sulfonic acid resin. The ion exchange resin has a cross-linked structure and is insoluble in water. Known sulfonic acid-type ion exchange resins are of a gel-type or a macroporous-type. While both types of the ion exchange resins may be used for the purpose of the present invention, the use of a gel-type ion exchange resin is advisable because the activity thereof remains unchanged during use. The gel-type ion exchange resin generally has a degree of cross-linking (the amount of the cross-linking agent contained in the resin) of 10% by weight or less, preferably 5% by weight or less. Illustrative of suitable commercially available, gel-type ion exchange reins are Amberlite, Amberlyst (both manufactured by Rohm & Haas Company) and DIAION (manufactured by Mitsubishi Kasei Inc.).

The contact of the raw material phenol with the ion exchange resin may be carried out by passing the raw material phenol through a fixed layer of the ion exchange packed in a tower or by stirring a mixture of the phenol and the ion exchange resin in a vessel. The contact is generally performed at 45°–150° C., preferably 50°–100° C. for 5–200 minutes, preferably 15–60 minutes. It is preferred that the raw material phenol have a water content of 0.5% by weight or less, more preferably 0.1% by weight or less, for reasons of improved impurity removing effect. The removal of moisture from the raw material phenol may be effected by azeotropic distillation using a suitable known azeotrope agent.

By the contact with the ion exchange resin, the impurities such as benzofurane and derivatives thereof and aromatic aldehydes and derivatives thereof contained in the raw material phenol are converted into high boiling point substances with the ion exchange resin serving as a catalyst.

The raw material phenol which has been treated with the strong-acid ion exchange resin is then distilled to obtain purified phenol as a distillate, with high boiling point impurities formed in the previous treatment with the ion exchange resin being separated as distillation residues.

The distillation is performed under conditions so that the high boiling point impurities are not contained in the distillate. To achieve this purpose, it is preferable to perform the distillation at a temperature of 185° C. or less. At a temperature higher than 185° C., the high boiling point impurities tend to be decomposed and to contaminate the distillate. While the distillation may be carried out at any desired pressure, a reduced pressure of 50–600 Torr is preferably used. The thus obtained purified phenol has a an APHA color of 10 or less so that it does not adversely affect the hue of bisphenol A when used for washing the adduct of bisphenol A and phenol.

Any method may be adopted for washing the adduct with the purified phenol. For example, after completion of the crystallization for the formation of the crystalline adduct, the adduct is separated from the mother liquor in a solid-liquid separator such as a filtering device or a centrifuge. The purified phenol is fed to the solid-liquid separator for washing the adduct remaining therein. The resulting mixture is then separated into a washed adduct and used phenol. Alternatively, the adduct obtained in the solid-liquid separator is transferred to a washing tank where the adduct is washed with the purified phenol with stirring. The washed adduct is again separated with the solid-liquid separator from the used phenol. In either case, the purified phenol is generally used in an amount of 30–1000 parts by weight, preferably 100–300 parts by weight per 100 parts by weight of the crystalline adduct to be washed.

The crystalline adduct thus washed with the purified phenol is then decomposed to bisphenol A and phenol for the recovery of bisphenol A. This can be effected by any known manner such as by distillation, extraction or steam stripping. The bisphenol A thus obtained from the adduct has a good hue and a high purity and is substantially colorless because of the use of specifically purified phenol in the washing of the adduct. Further, since the purified phenol is free of a solvent, it can be recycled as such to any desired step such as the reaction step for the reaction with acetone.

The purified phenol obtained by the above specific treatment has a high purity and an excellent hue and is suitably used as a raw material for the production of alkyl phenols, phenol resins or the like phenol derivatives. By admixing the purified phenol with 0.001–0.01% by weight of oxalic acid or citric acid, the hue thereof is prevented from being deteriorated for a long period of storage.

The following examples will further illustrate the present invention. Percentage and ppm are by weight. The APHA number referred to in the examples is measured in accordance with the method specified in ASTM D 1686, "Standard Test Method for Color of Solid Aromatic Hydrocarbons and Related Materials in the Molten State".

Example 1

Preparation of Crystalline Adduct

Acetone was reacted with phenol in the presence of an acid catalyst to obtain a mixture having an APHA color of 50 and containing bisphenol A, phenol and impurities. The mixture was then cooled to obtain a slurry containing a crystalline adduct of bisphenol A and phenol. The slurry was filtered under a reduced pressure to separate the crystalline adduct as a crude product.

Preparation of Purified Phenol

Commercially available phenol (water content: 0.1%, impurity content: 0.05%) was contacted with a sulfonic acid-type cation exchange resin (Amberlite IR-118H+, manufactured by Rohm & Haas Company) at 80° C. for 50 minutes. The thus treated phenol was then distilled at a distillation tower bottom temperature of 175° C., a tower top pressure of 560 Torr to obtain purified phenol whose color in the molten state had an APHA color of 6.

Preparation of Bisphenol A

The crude adduct obtained above was washed with 2.5 times the weight of the above purified phenol. The washed adduct was subjected to steam stripping at a temperature of 175° C., a pressure of 25 Torr for 30 minutes to isolate bisphenol A having excellent hue and an APHA color of 15 at 175° C.

Comparative Example 1

A portion of the crude adduct obtained in Example 1 was decomposed at 190° C. to recover phenol. Another portion of the crude adduct was washed with 2.5 times the weight of the thus recovered phenol. The washed adduct was subjected to steam stripping at a temperature of 175° C., a pressure of 25 Torr for 30 minutes to isolate bisphenol A having an APHA color of 20 at 175° C. When this bisphenol A was allowed to stand at 175° C. for 5 hours in air, the APHA color thereof was increased to 80.

Comparative Example 2

Purified phenol was prepared in the same manner as that in Example 1 except that the distillation tower bottom temperature was maintained at 200° C. The crude adduct obtained in Example 1 was washed with this purified phenol and the washed adduct was subjected to steam stripping in the same manner as that in Example 1 to obtain Bisphenol A whose APHA color at 175° C. was 30.

Example 2

Commercially available phenol (water content: 0.07%, impurity content: 430 ppm) was contacted with a sulfonic acid-type cation exchange resin (Amberlite IR-118H+, manufactured by Rohm & Haas Company) at 80° C. for 20 minutes. The thus treated phenol was then distilled at a distillation tower bottom temperature of 173° C., a tower top pressure of 560 Torr to obtain purified phenol.

Comparative Example 3

Example 2 was repeated in the same manner as described except that commercially available phenol having a water content of 0.73% and impurity content of 430 ppm was used as the raw material. The impurity content, benzofuran content and APHA color of the raw material phenol, intermediate phenol (after treatment with the ion exchange resin) and purified phenol are shown in Table 1.

TABLE 1

| | Raw Material Phenol | Intermediate Phenol | Purified Phenol |
|---|---|---|---|
| Example 2 | | | |
| Impurity Content (ppm) | 430 | 1205 | 5 |
| Benzofuran Content (ppm) | 310 | —*1 | —*1 |
| APHA Color | 20 | 30 | 5 |
| Comparative Example 3 | | | |
| Impurity Content (ppm) | 430 | 796 | 115 |
| Benzofuran Content (ppm) | 310 | 42 | 25 |
| APHA Color | 20 | 30 | 10 |

-*1: Not detected.

Example 3

Commercially available phenol (water content: 0.07%, impurity content: 430 ppm) was continuously passed through a column packed with a sulfonic acid-type cation exchange resin (Amberlite IR-118H+, manufactured by Rohm & Haas Company) at 80° C. with residence time of 20 minutes for 1000 hours. No benzofuran was detected in the treated phenol obtained throughout the 1000 hours running.

Example 4

Preparation of Crystalline Adduct

Acetone was reacted with phenol in the presence of an acid catalyst to obtain a mixture (APHA color 50) containing bisphenol A, phenol and impurities. A portion of the mixture was then cooled to obtain a slurry containing a crystalline adduct of bisphenol A and phenol. The slurry was filtered under a reduced pressure to separate the crystalline adduct as a crude product.

Preparation of Purified Phenol

Another portion of the above mixture was distilled to obtain phenol which in turn was dehydrated to obtain raw material phenol having a water content of 0.1%. This raw material phenol was contacted with a sulfonic acid-type cation exchange resin (Amberlite IR-118H+, manufactured by Rohm & Haas Company) at 80° C. for 50 minutes. The thus treated phenol was then distilled at a distillation tower bottom temperature of 175° C., a tower top pressure of 560 Torr to obtain purified phenol whose APHA color was 5.

Preparation of Bisphenol A

The crude adduct obtained above was washed with 2.5 times the weight of the above purified phenol. The washed adduct was subjected to steam stripping at a temperature of 175° C., a pressure of 25 Torr for 30 minutes to isolate bisphenol A having excellent hue and an APHA color of 10–15 at 175° C. When this bisphenol A was allowed to stand at 175° C. for 5 hours in air, the APHA color thereof was increased to 30.

What is claimed is:

1. A process for the production of bisphenol A, comprising the steps of:
   (a) reacting acetone with a stoichiometrically excess amount of phenol to obtain a bisphenol A-containing product;
   (b) crystallizing said product to obtain a crystalline adduct of bisphenol A and phenol;

(c) providing raw material phenol which contains an impurity convertible to a high boiling point material having a boiling point of higher than 185° C. upon being heated at a temperature higher than the melting point of phenol;

(d) contacting said raw material phenol with a gel-type sulfonic acid-type cation exchange resin having a degree of cross-linking of 10% by weight or less at a temperature and for a period of time sufficient to convert at least part of said impurity into said high boiling point material and to obtain treated phenol;

(e) distilling said treated phenol at a temperature of 185° C. or less to separate purified phenol, as distillate, from said high boiling point material;

(f) washing said adduct with said purified phenol; and (g) decomposing said washed adduct to obtain bisphenol A.

2. A process as claimed in claim 1, wherein said raw material phenol includes at least one member selected from the group consisting of phenol of an industrial use grade, phenol recovered from step (a), phenol recovered from step (b) and phenol recovered from step (f).

3. A process as claimed in claim 1, wherein said cation exchange resin has a degree of cross-linking of 5% by weight or less.

* * * * *